(12) United States Patent
Wang et al.

(10) Patent No.: US 11,175,259 B2
(45) Date of Patent: Nov. 16, 2021

(54) SENSING DEVICE AND ION DETECTION METHOD

(71) Applicant: National Tsing Hua University, Hsinchu (TW)

(72) Inventors: Yu-Lin Wang, Hsinchu (TW); Yi-Ting Chen, Hsinchu (TW); Revathi Sukesan, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 18 days.

(21) Appl. No.: 15/886,842

(22) Filed: Feb. 2, 2018

(65) Prior Publication Data
US 2019/0094176 A1 Mar. 28, 2019

(30) Foreign Application Priority Data
Sep. 26, 2017 (TW) .................................. 106133023

(51) Int. Cl.
| | | |
|---|---|---|
| *G01N 27/414* | (2006.01) | |
| *G01N 33/18* | (2006.01) | |
| *G01N 33/20* | (2019.01) | |
| *G01N 27/333* | (2006.01) | |
| *H01L 29/778* | (2006.01) | |

(52) U.S. Cl.
CPC ..... *G01N 27/4148* (2013.01); *G01N 27/4143* (2013.01); *G01N 33/1813* (2013.01); *G01N 33/20* (2013.01); *G01N 27/333* (2013.01); *H01L 29/7787* (2013.01)

(58) Field of Classification Search
CPC . G01N 27/414; G01N 27/333; G01N 33/1813
See application file for complete search history.

(56) References Cited

U.S. PATENT DOCUMENTS

| | | | |
|---|---|---|---|
| 4,514,263 | A | 4/1985 | Janata |
| 8,828,713 | B2 | 9/2014 | Ren et al. |
| 2008/0134759 | A1* | 6/2008 | Mohammed-Brahim ................... G01N 27/4143 73/31.06 |
| 2017/0059514 | A1* | 3/2017 | Hoffman ............ G01N 33/5438 |
| 2017/0082570 | A1* | 3/2017 | Takechi ................. C12Q 1/006 |
| 2017/0241944 | A1* | 8/2017 | Schneider ............ G01N 27/414 |

FOREIGN PATENT DOCUMENTS

| | | |
|---|---|---|
| CN | 101048656 | 10/2007 |
| CN | 101676714 | 3/2010 |
| CN | 102338767 | 2/2012 |
| CN | 104880501 | 9/2015 |

(Continued)

OTHER PUBLICATIONS

Wang, CN 107102028 machine translation version (Year: 2017).*

(Continued)

*Primary Examiner* — Luan V Van
*Assistant Examiner* — Caitlyn Mingyun Sun
(74) *Attorney, Agent, or Firm* — JCIPRNET (57) ABSTRACT

A sensing device including a transistor, at least one response electrode, and a selective membrane is provided. The transistor includes a gate end, a source end, a drain end, and a semiconductor layer, wherein the source end and the drain end are located on the semiconductor layer, and the gate end is located between the source end and the drain end. The at least one response electrode is disposed opposite to the gate end of the transistor and spaced apart from the transistor. The selective membrane is located on the at least one response electrode or on the transistor.

17 Claims, 8 Drawing Sheets

(56) References Cited

FOREIGN PATENT DOCUMENTS

| CN | 107024522 | 8/2017 |
|---|---|---|
| CN | 107102028 | 8/2017 |
| CN | 107121475 | 9/2017 |
| CN | 107121476 | 9/2017 |
| CN | 107121556 | 9/2017 |
| TW | I435078 | 4/2014 |
| TW | I565946 | 1/2017 |
| TW | 201730556 | 9/2017 |
| WO | 2016185679 | 11/2016 |

OTHER PUBLICATIONS

Hokkaido, CN101287986 machine translation version (Year: 2008).*
Revathi Sukesana, et al., "Mercury Selective GaN HEMT Sensor For Dynamic Water Quality Monitoring," ECS Transactions, vol. 80, Oct. 2017, pp. 953-957.
"Office Action of Taiwan Counterpart Application", dated Jul. 17, 2018, p. 1-p. 5.
"Office Action of China Counterpart Application", dated Jul. 31, 2020, p. 1-p. 11.
Mohsen Asadnia, et al., "Mercury(II) selective sensors based on AlGaN/GaN transistors," Analytica Chimica Acta, vol. 943, Nov. 2016, pp. 1-8.
Peng Li, et al., "Graphene field-effect transistors with tunable sensitivity for high performance Hg (II) sensing," Applied Physics Letters, vol. 109, Oct. 2016, pp. 1-6.
Peng Li, et al., "Ultra-sensitive suspended atomically thin-layered black phosphorus mercury sensors," Biosensors and Bioelectronics, vol. 98, Jun. 2017, pp. 68-75.

* cited by examiner

SENSING DEVICE AND ION DETECTION METHOD

CROSS-REFERENCE TO RELATED APPLICATION

This application claims the priority benefit of Taiwan application serial no. 106133023, filed on Sep. 26, 2017. The entirety of the above-mentioned patent application is hereby incorporated by reference herein and made a part of this specification.

BACKGROUND OF THE INVENTION

1. Field of the Invention

The invention relates to a sensing device and a detection method, and more particularly, to a sensing device and an ion detection method.

2. Description of Related Art

Most of heavy metal elements (e.g., lead (Pb), mercury (Hg), cadmium (Cd), chromium (Cr) or metalloid arsenic (As)) in the human body have no physiological function but can produce toxic effects to the human body. Also, due to poor metabolism of the human body for the heavy metals, those heavy metals can be easily accumulated in the human body, causing serious illness. For instance, in the human body, a lead content above the standard value may cause dementia; and a mercury content above the standard value may result in great damage to the brain optic nerve. Therefore, it is important to detect the heavy metal content in water so as to ensure the safety of drinking water.

Currently, equipments for detecting the heavy metal content in water are, for example, an inductively coupled plasma-atomic emission spectrometer (ICP-AES), an inductively coupled plasma-mass spectrometer (ICP-MS) or an ion-selective electrode (ISE). As expensive huge lab instruments with complex operating method that requires analysis to be done by professionals, the ICP-AES and the ICP-MS are unable to detect samples on site and is unsuitable for general use. In spite of portability and capability of detecting on site, the ISE has a detection limit of around 500 ppb, which is inadequate to confirm whether or not the heavy metal content in water meets to a standard value specified in the current regulations. For instance, in the case of lead, with the regulations in Taiwan which specified that a lead ion content in water needs to be less than approximately 50 ppb (approximately $2.42 \times 10^{-7}$M), the ISE is unable to confirm whether the lead ion content in water exceeds the standard value since the detection limit is way higher than the standard value of lead ion. Besides, the overall detection cost is still overly high because the ISE needs to perform the detection in combination with reference electrodes.

In light of the above, how to develop a sensing device suitable for real-time detection on site with a low detection limit and a high sensitivity is one of the important issues to be addressed by those skilled in the art.

SUMMARY OF THE INVENTION

The invention provides a sensing device and an ion detection method, which provide characteristics of the low detection limit and the high sensitivity, and are suitable for real-time detection on site.

The invention provides a sensing device, which includes a transistor, at least one response electrode, and a selective membrane. The transistor includes a gate end, a source end, a drain end, and a semiconductor layer, wherein the source end and the drain end are located on the semiconductor layer, and the gate end is located between the source end and the drain end. The at least one response electrode is disposed opposite to the gate end of the transistor and spaced apart from the transistor. The selective membrane is located on the at least one response electrode or on the transistor.

According to an embodiment of the invention, an electric field between the at least one response electrode and the gate end of the transistor is F when a voltage is applied to the at least one response electrode, and F≥1 mV/cm.

According to an embodiment of the invention, the at least one response electrode is a plurality of response electrodes, and the response electrodes are spaced apart from each other.

According to an embodiment of the invention, a plurality of switch circuits are further included. Each of the response electrodes is connected to the corresponding switch circuit.

According to an embodiment of the invention, the at least one response electrode is separately disposed above the gate end of the transistor.

According to an embodiment of the invention, the at least one response electrode and the gate end of the transistor are located on a same plane.

According to an embodiment of the invention, the transistor includes a high electron mobility transistor, a silicon-based field effect transistor, a nanowire field effect transistor, a carbon nanotube field effect transistor, a graphene field effect transistor or a molybdenum disulfide field effect transistor.

According to an embodiment of the invention, the selective membrane includes an ion selective membrane, a molecular selective membrane, a gas selective membrane or a combination thereof.

According to an embodiment of the invention, the ion selective membrane includes an ionophore, an ionic complex, a plasticizer, a polymeric material or a combination thereof.

The invention also provides an ion detection method, which includes the following steps. A sensing device is provided, wherein the sensing device includes a transistor, at least one response electrode and an ion selective membrane, the at least one response electrode is disposed opposite to the gate end of the transistor and spaced apart from the transistor, and the selective membrane is located on the at least one response electrode or on the transistor. A test solution is placed onto the ion selective membrane. A voltage is applied to the at least one response electrode to generate an electric field between the at least one response electrode and the gate end of the transistor, and a current generated from the transistor is measured to obtain an ion content of the test solution.

According to an embodiment of the invention, the electric field is F, and F≥1 mV/cm.

According to an embodiment of the invention, the at least one response electrode is a plurality of response electrodes, and the response electrodes are spaced apart from each other.

According to an embodiment of the invention, the sensing device further includes a plurality of switch circuits. Each of the response electrodes is connected to the corresponding switch circuit.

According to an embodiment of the invention, the at least one response electrode is separately disposed above the gate end of the transistor.

According to an embodiment of the invention, the at least one response electrode and the gate end of the transistor are formed on a same plane.

According to an embodiment of the invention, the transistor includes a high electron mobility transistor, a silicon-based field effect transistor, a nanowire field effect transistor, a carbon nanotube field effect transistor, a graphene field effect transistor or a molybdenum disulfide field effect transistor.

According to an embodiment of the invention, the ion selective membrane includes an ionophore, an ionic complex, a plasticizer, a polymeric material or a combination thereof.

Based on the above, in the sensing device and the ion detection method proposed by the invention, because the response electrode is disposed opposite to the gate end of the transistor and spaced apart from the transistor, the sensing device can have the characteristics of the low detection limit and the high sensitivity. Further, because the selective membrane is located on the response electrode or on the transistor, the sensing device can provide a high selectivity for the test object to be measured.

To make the above features and advantages of the disclosure more comprehensible, several embodiments accompanied with drawings are described in detail as follows.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

Reference will now be made in detail to the present preferred embodiments of the invention, examples of which are illustrated in the accompanying drawings. Wherever possible, the same reference numbers are used in the drawings and the description to refer to the same or like parts.

The invention will be described more comprehensively below with reference to the drawings for the embodiments. However, the invention may also be implemented in different forms rather than being limited by the embodiments described in the invention. Thicknesses of layer and region in the drawings are enlarged for clarity. The same reference numbers are used in the drawings and the description to indicate the same or like parts, which are not repeated in the following embodiments. Further, the language used to describe the directions such as up, down, left, right, front, back or the like in the reference drawings is regarded in an illustrative rather than in a restrictive sense. Thus, the language used to describe the directions is not intended to limit the scope of the invention.

Figure 1:
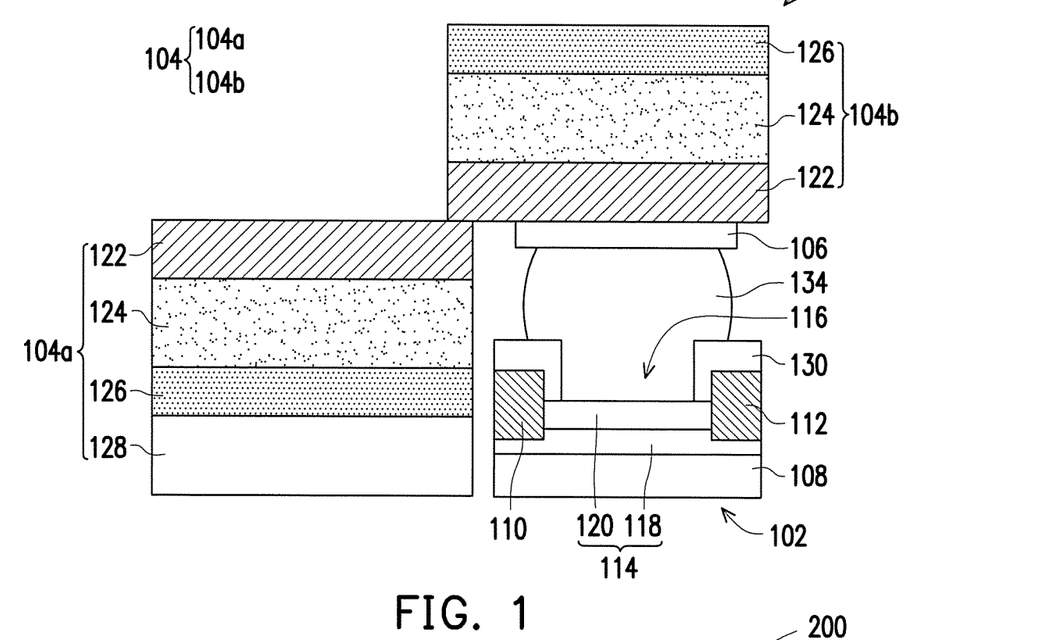
FIG. 1 is a side view of a sensing device according to an embodiment of the invention.
Figure 2:
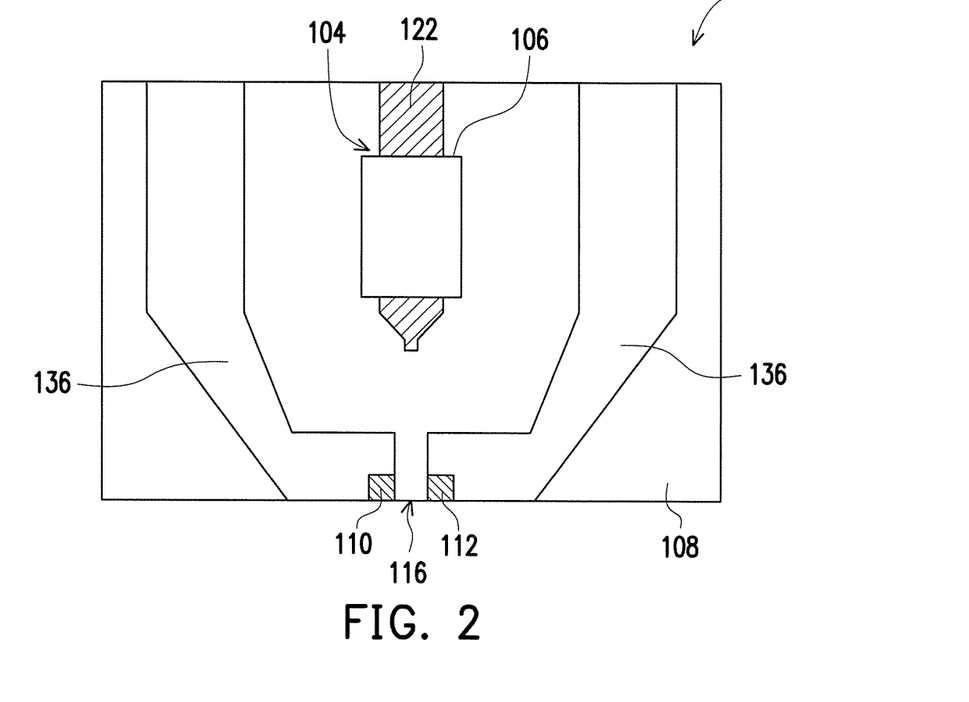
FIG. 2 is a top view of a sensing device according to another embodiment of the invention.

FIG. 1 is a side view of a sensing device according to an embodiment of the invention. FIG. 2 is a top view of a sensing device according to another embodiment of the invention.

With reference to FIG. 1, a sensing device 100 includes a transistor 102, at least one response electrode 104 and a selective membrane 106. In some embodiments, the sensing device 100 is applicable to detect an ion content in a test solution, but the invention is not limited thereto. In other embodiments, the sensing device 100 may also serve as a gas sensor or other suitable sensors.

The transistor 102 may include a substrate 108, a source end 110, a drain end 112, a semiconductor layer 114 and a gate end 116. The transistor 102 is, for example, a high electron mobility transistor (HEMT), a silicon-based field effect transistor, a nanowire field effect transistor, a carbon nanotube field effect transistor, a graphene field effect transistor or a molybdenum disulfide field effect transistor.

The semiconductor layer 114 is located on the substrate 108. A material of the substrate 108 is, for example, silicon, sapphire or a combination thereof. A material of the semiconductor layer 114 is, for example, GaN, AlInN, AlGaN or a combination thereof. In some embodiments, the transistor 102 is the high electron mobility transistor, in which the semiconductor layer 114 is composed of a GaN layer 118 and an AlInN layer 120 located thereon. In this case, due to a low dimensional heterogeneous structure interface between the GaN layer 118 and the AlInN layer 120, the transistor 102 can provide an excellent carrier transmission characteristic. In some other embodiments, other materials with piezoelectricity such as AlGaN may also be used to replace the AlInN layer 120. In other words, in the semiconductor layer 114, materials of layers formed on the GaN layer 118 are not limited only to be AlInN, and instead, the other materials with piezoelectricity may also be used. In some embodiments, a size of the AlInN layer 120 is less than that of the GaN layer 118. In other words, a part of a top surface of the GaN layer 118 is exposed to be in contact with the source end 110 and the drain end 112 located thereon. In some embodiments, the semiconductor layer 114 may be formed on the substrate 108 by a physical vapor deposition (PVD) or a chemical vapor deposition (CVD).

The source end 110 and the drain end 112 are located on the semiconductor layer 114, and the gate end 116 is located between the source end 110 and the drain end 112. In some embodiments, the source end 110 and the drain end 112 are respectively located on two opposite sidewalls of the AlInN layer 120 and on the top surface of the GaN layer 118. In some embodiments, materials of the source end 110 and the drain end 112 may include one or more than one conductive material, and said conductive material may be, for example, a metallic material, a metallic compound or a combination thereof. The metallic material may be, for example, Ti, Al, Ni, Au, W or a combination thereof; the metallic compound may be, for example, TiN, TiW, TiWN, WN or a combination thereof. A forming method of the source end 110 and the drain end 112 may be, for example, a chemical vapor deposition, a physical vapor deposition or other suitable forming methods.

The response electrode 104 is disposed opposite to the gate end 116 of the transistor 102 and spaced apart from the transistor 102, and the response electrode 104 is not electrically connected to the gate end 116. In some embodiments, when a voltage is applied to the response electrode 104, an electric field F is generated between the response electrode 104 and the gate end 116 of the transistor 102. In some embodiments, the electric field F is greater than or equal to 1 millivolt/centimeter (F≥1 mV/cm). In this way, when the applied electric field F is within aforesaid range, the sensing device 100 is capable of surpassing Nernst limit to provide lower detection limit and higher sensitivity. In addition, in some embodiments, the response electrode 104 may include a response layer 122, a silicon nitride layer 124 and a base 126.

The response layer 122 is disposed opposite to the gate end 116 of the transistor 102 and spaced apart from the transistor 102 above the gate end 116 of the transistor 102. In some embodiments, the response layer 122 may include materials such as a metal, a nano material or a conductive polymer to improve sensitivity, detection limit, stability or selectivity for the sensing device 100. For instance, the response layer 122 may contain metal Bi or a carbon nanotube to improve the sensitivity or the detection limit for detecting heavy metal ion; the response layer 122 may also be composed of metal with more stable chemical property such as Au or Pt, so as to improve the stability of the sensing device 100.

The silicon nitride layer 124 is located between the response layer 122 and the base 126. In this way, the silicon nitride layer 124 can block electrons generated by the response layer 122 in the detection from being transferred to the base 126, so as to reduce measurement deviation. A material of the base 126 is, for example, silicon, but the invention is not limited thereto.

In some embodiments, the response electrode 104 may be composed of a first sub-electrode 104a and a second sub-electrode 104b, which are structurally identical and oppositely connected to each other. For example, the first sub-electrode 104a is disposed on a glass substrate 128 in a direction away from the base 126 with respect to the response layer 122, and a sum of heights of the first sub-electrode 104a and the glass substrate 128 is greater than a height of the transistor 102. Then, the response layer 122 of the second sub-electrode 104b and the response layer 122 of the first sub-electrode 104a are connected to each other by having the response layer 122 of the second sub-electrode 104b protruded out of the first sub-electrode 104a, such that the response layer 122 of the second sub-electrode 104b is located above the gate end 116 of the transistor 102 and a gap interval is formed between the response layer 122 of the second sub-electrode 104b and the gate end 116. That is to say, the response electrode 104 is separately disposed above the gate end 116 of the transistor 102. In some other embodiments, the response electrode 104 may also be formed as one piece.

The selective membrane 106 is located on the response electrode 104. In this way, the selective membrane 106 may be used to allow a test object to be measured to approach a surface of the response electrode 104 or prevent an interference substance from approaching the surface of the response electrode 104, such that the sensing device 100 can provide the high selectivity for the test object to be measured. The selective membrane 106 can cover the entire response electrode 104 or cover a part of the response electrode 104, and the invention is not limited thereto. The selective membrane 106 may be, for example, an ion selective membrane, a molecular selective membrane, a gap molecular selective membrane or a combination thereof. The ion selective membrane may be an anion selective membrane, a cation selective membrane or a combination thereof. The gas molecular selective membrane may include n-type or p-type semiconductor materials. For instance, when the gas molecular selective membrane includes the n-type material, the sensing device constituted by the same may be used to detect gases including NO, $NO_2$, $NH_3$, Hz, $SO_2$, $H_2S$, $O_2$, $O_3$, CO, $CH_4$, $C_2H_4$, $C_2H_2$ or $Cl_2$. In some embodiments, the selective membrane 106 may be an ion selective membrane including an ionophore, an ionic complex, a plasticizer, a polymeric carrier or a combination thereof. The ionophore may be a metal ionophore such as lead ionophore IV; the ionic complex may be Potassium tetrakis(4-chlorophenyl)borate; the plasticizer may be 2-Nitrophenyl octyl ether (2NOE); the polymeric carrier may be polymer polyvinyl chloride (PVC). However, the invention is not limited thereto. Other suitable materials may also be selectively used according to different detection targets.

In some embodiments, top surfaces and sidewalls of the source end 110 and the drain end 112 may also be selectively covered by a protective layer 130 to improve a stability of the transistor 102. A material of the protective layer 130 is, for example, a photoresist material.

FIG. 2 is a top view of a sensing device according to another embodiment of the invention. A sensing device 200 shown in FIG. 2 is similar to the sensing device 100 shown in FIG. 1, the difference between the two is that, the response electrode 104 and the gate end 116 of the transistor 102 are located on a same plane, and a AlGaN layer is formed on the GaN layer 118 of the transistor 102. Detailed description regarding the rest of identical or similar components has been provided above, which is not repeated hereinafter.

With reference to FIG. 2, in the sensing device 200, the response electrode 104 can be located on the same plane with the gate end 116 of the transistor 102 and disposed opposite to and spaced apart from each other by extending the substrate 108 of the transistor 102 and disposing the response electrode 104 on the substrate 108. In this embodiment, the selective membrane 106 covers a part of the response electrode 104, and the source end 110 and the drain end 112 are connected to external electronic devices (not shown) respectively by a wiring 136.

Figure 3:
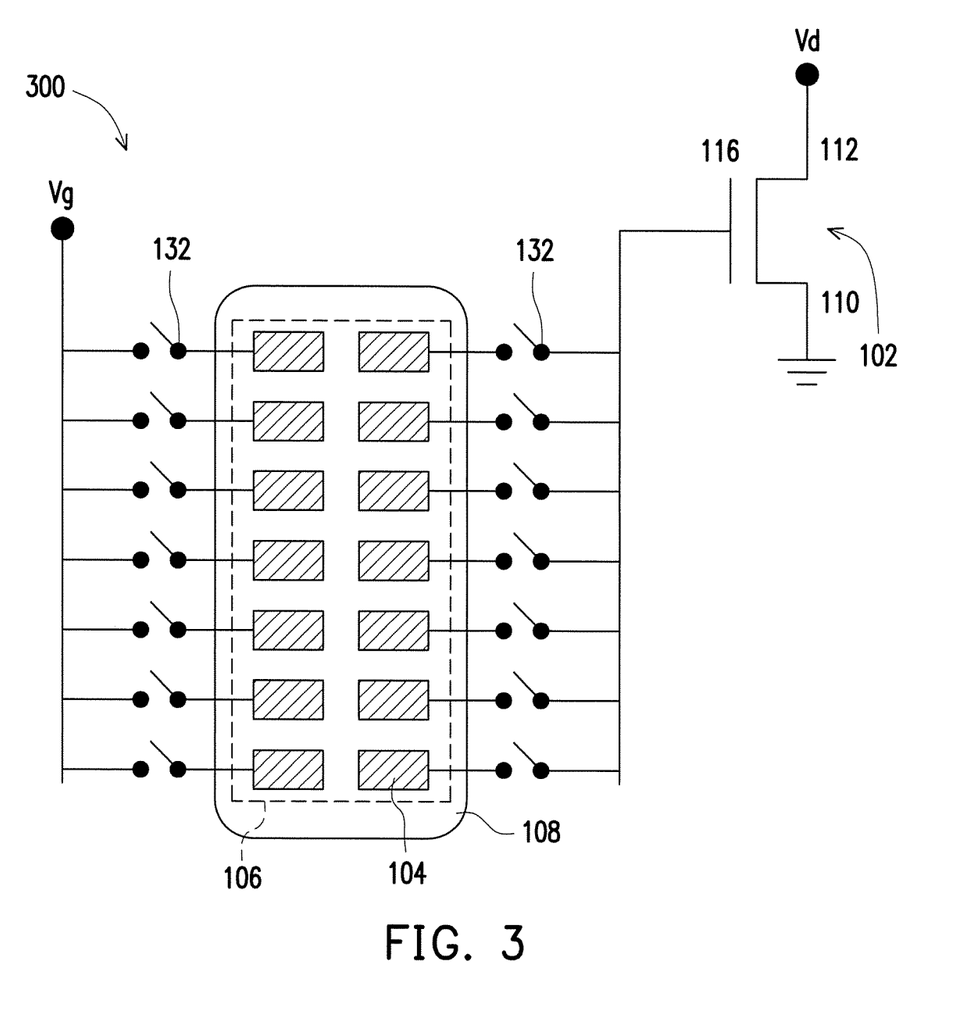
FIG. 3 is a top view of a sensing device according to yet another embodiment of the invention.

FIG. 3 is a top view of a sensing device according to yet another embodiment of the invention. A sensing device 300 shown in FIG. 3 is similar to the sensing device 200 shown in FIG. 2, the difference between the two is that, the sensing device 300 has a plurality of response electrodes 104, and the response electrodes 104 are disposed on the substrate 108 and spaced apart from each other. Detailed description regarding the rest of identical or similar components has been provided above, which is not repeated hereinafter.

With reference to FIG. 3, the sensing device 300 includes the response electrodes 104, and the response electrodes 104 correspond to the same transistor 102. In this way, the sensing device 300 can simultaneously perform multiple detections on the same or different species of analytes. As such, not only can a reliability of the detection result be improved, a time required by the detection may be reduced. In addition, because the response electrodes 104 share the same transistor 102 and the next detection may be performed simply by replacing the used response electrode 104, a cost required by the detection may be lowered. In some embodiments, the sensing device 300 further includes a plurality of switch circuits 132, and each of the response electrodes 104 is connected to the corresponding switch circuit 132. Accordingly, the desired response electrode 104 to be used may be selectively controlled such that the sensing device 300 is applicable to various measuring means. For example, the same analyte may be detected at different times, so as to observe a variation in concentration and time. In some embodiments, the switch circuits 132 are located on two opposite sides of the response electrodes 104. The switch circuits 132 located on one side of the response electrodes 104 are connected to a gate voltage Vg; and the switch circuits 132 located on the other side of the response electrodes 104 are connected to the gate end 116. Further, in the measurement, the source end 110 of the transistor 102 is connected to the ground, and a drain voltage Vd is applied to the drain end 112.

The invention also provides an ion detection method, which is described below by using the sensing device 100 in the foregoing embodiment for an ion detection, but the invention is not limited thereto. In other embodiments, the sensing devices 200 and 300 in other foregoing embodiments may also be used. Further, detailed description regarding the connection relationship, the material, the manufacturing process and the effect of each component in the sensing device 100 has been provided above, which is not repeated hereinafter.

With reference to FIG. 1, the ion detection method includes the following steps. First of all, the sensing device 100 is provided, wherein the sensing device 100 includes the transistor 102, the response electrode 104 and the ion selective membrane (i.e., the selective membrane 106). The response electrode 104 is disposed opposite to the gate end 116 of the transistor 102 and spaced apart from the transistor 102, and the ion selective membrane is formed on the response electrode 104.

Next, a test solution 134 is placed onto the ion selective membrane to be in adequately contact with the ion selective membrane. A volume of the test solution 134 is not particularly limited as long as the test solution 134 can be in contact with the ion selective membrane (i.e., the selective membrane 106) and the semiconductor layer 114 or the gate end 116 of the transistor 102 (as shown in FIG. 1). In some embodiments, before the test solution 134 is placed onto the ion selective membrane, a pretreatment process may also be performed on the test solution 134 so as to remove the interference substance in the test solution 134.

Then, a voltage is applied to the response electrode 104 to generate the electric field F between the response electrode 104 and the gate end 116 of the transistor 102, and a current generated from the transistor 102 is measured to obtain an ion content of the test solution 134. In some embodiments, the applied voltage may be a pulse voltage. Sizes of pulse width and height of the pulse voltage may be adjusted according to a desired detection time to be analyzed by the user and a voltage magnitude required by the detection. For instance, the applied voltage may be a single pulse (drain voltage=2V; gate voltage=0.5V; gate pulse width=0.5 µs) or a biphasic pulse (drain voltage=2V; gate voltage=0.5V; gate cycle pulse width=1 ms). In some embodiments, the electric field F is greater than or equal to 1 millivolt/centimeter (F mV/cm). In this way, when the applied electric field F is within aforesaid range, the sensing device 100 is capable of surpassing Nernst limit to provide the lower detection limit and the higher sensitivity.

In some embodiments, the measured current generated from the transistor may be selectively converted. For example, an integral conversion may be performed on the detected current with respect to the pulse width. In this case, the integral of current versus time is calculated so a total amount of charge accumulated by the source end 110 of the transistor 102 within a specific time may be obtained.

Based on the foregoing embodiments, it can be known that, in the sensing device and the ion detection method proposed in the foregoing embodiments, because the response electrode is disposed opposite to the gate end of the transistor and spaced apart from the transistor, the sensing device can have the characteristics of the low detection limit and the high sensitivity. Further, because the selective membrane is located on the response electrode or on the transistor, the sensing device can provide the high selectivity for the test object to be measured.

Hereinafter, the ion detection method and characteristics thereof are described in detail by experimental examples. However, the experimental examples below are not intended to limit the invention. It should be noted that, the following experimental examples are described by measuring the amount of lead ion ($Pb^{2+}$) or mercury ion ($Hg^{2+}$) in the test solution for example, but the invention is not limited thereto. Further, a gain represents a difference between a balanced current value and an initial current value (i.e., a background current) in the following experiments (i.e., the balanced current value−the initial current value=the gain). The initial current value can represent a current value obtained by applying an initial voltage to the response electrode 104. In the present embodiment, the initial voltage may be less than the gate voltage, but the invention is not limited thereto. The balanced current value can represent a current value obtained after the gate voltage Vg is applied to the response electrode 104 for a certain time. The ion selective membrane used in the following experiments contains 1 w % lead ionophore IV, 0.35 w % Potassium tetrakis(4-chlorophenyl) borate, 65.65 w % 2-Nitrophenyl octyl ether (2NOE), and 33 w % polymer polyvinyl chloride (PVC).

EXPERIMENTAL EXAMPLES

Experiment 2 to Experiment 5 are ion concentration detections with the sensing device 200 as exemplary embodiments. Experiment 6 and Experiment 7 are ion concentration detections with the sensing device 300 as exemplary embodiments.

Experiment 1

Figure 4:
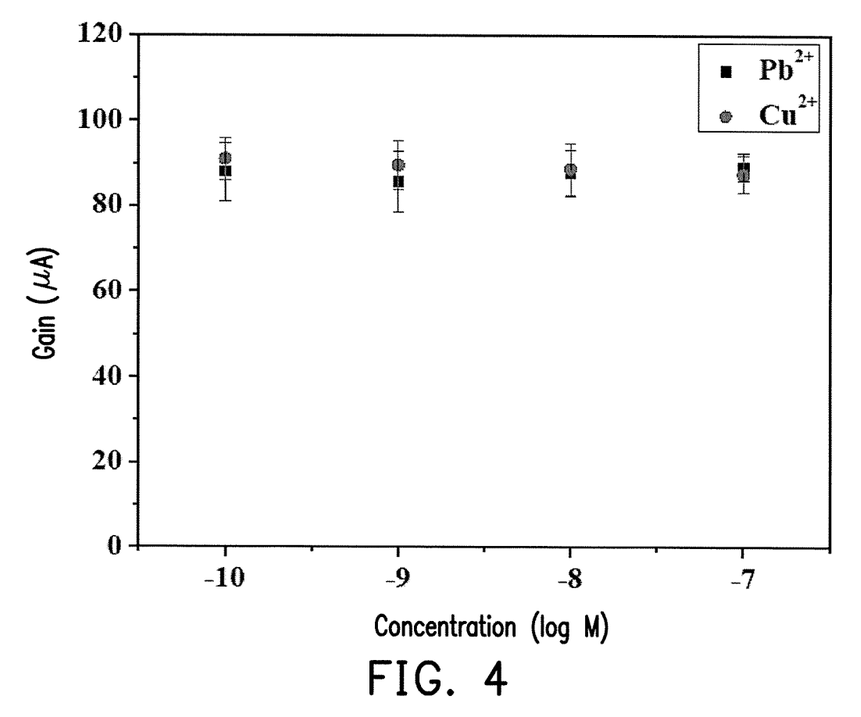
FIG. 4 is a gain ($\mu$A)-concentration (log M) graph obtained by detecting different concentrations of lead ion and cooper ion by a sensing device not having an ion selective membrane in Experiment 1.

FIG. 4 is a gain (µA)-concentration (log M) graph obtained by detecting different concentrations of lead ion ($Pb^{2+}$) and cooper ion ($Cu^{2+}$) by a sensing device not having an ion selective membrane in Experiment 1.

Test solutions used in Experiment 1 are test solutions containing different lead ion and copper ion concentrations, which are prepared by separately dissolving different amounts of lead nitrate and copper sulfate by a phosphate buffer solution at pH 7 diluted 100 times (0.01×PBS), wherein the lead ion and copper ion concentrations are $10^{-9}$M, $10^{-8}$M, $10^{-7}$M, $10^{-6}$M and $10^{-5}$M, respectively. The experiment result is shown in FIG. 4 with the concentrations represented in log values.

With reference to FIG. 4, as the concentration of lead ion and copper ion becomes higher, the gain measured by the sensing device show no significant change. In other words, in the case where the sensing device does not include the ion selective membrane, a concentration variation in the solution cannot be measured.

Experiment 2

Figure 5:
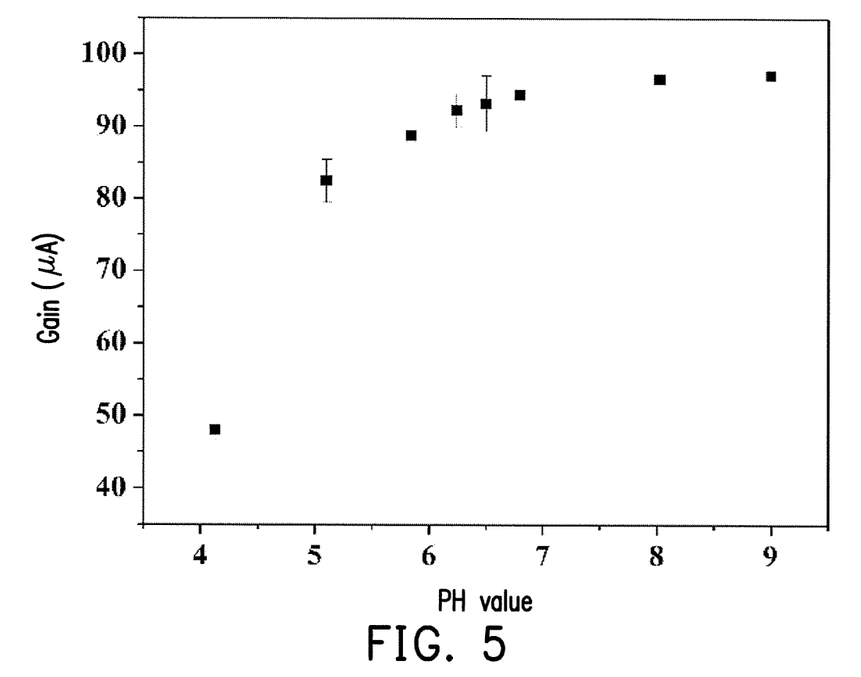
FIG. 5 is a gain-pH value graph obtained by performing an interference test on buffer solutions with different pH values by the sensing device in an embodiment of the invention in Experiment 2.

FIG. 5 is a gain-pH value graph obtained by performing an interference test on buffer solutions with different pH values by the sensing device in an embodiment of the invention in Experiment 2.

Experiment 2 adopts phosphate buffer solutions diluted 100 times with different pH values as test solutions, wherein the pH values are 4.13, 5.1, 5.84, 6.24, 6.5, 6.8, 8.02 and 9, respectively, and the experiment result is shown in FIG. 5.

With reference to FIG. 5, a variation of the gain becomes smaller as the pH value becomes higher, and the gain measured by the sensing device is almost unchanged after the pH value is greater than 6.8. In other words, in the case where the pH value of the test solution is greater than 6.8, the gain is not affected by a variation of the pH value. Therefore, with the ion detection performed in this pH environment, it can be ensured that the measured variation of the gain comes from a variation of the ion concentration rather than the variation of the pH value.

Experiment 3

Figure 6:
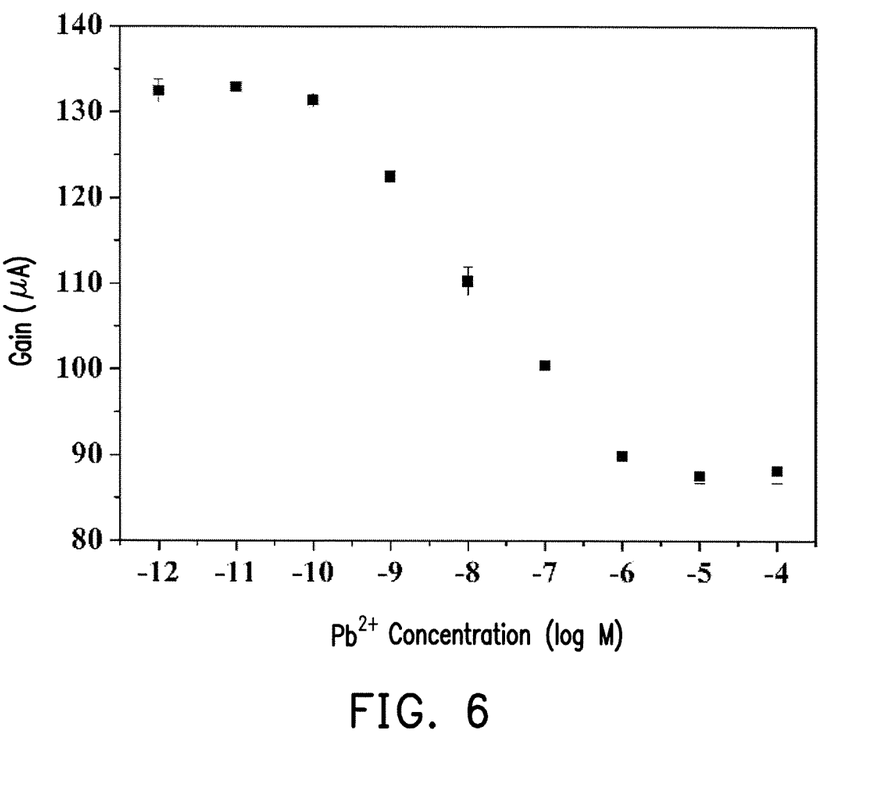
FIG. 6 is a gain-concentration graph obtained by detecting different concentrations of lead ion by the sensing device in an embodiment of the invention in Experiment 3.

FIG. 6 is a gain-concentration graph obtained by detecting different concentrations of lead ion by the sensing device in an embodiment of the invention in Experiment 3.

Test solutions used in Experiment 3 are test solutions containing different lead ion concentrations, which are prepared by dissolving different amounts of lead nitrate by a phosphate buffer solution at pH 7 diluted 100 times (0.01× PBS), wherein the lead ion concentrations are $10^{-12}$M, $10^{-11}$M, $10^{-10}$M, $10^{-9}$M, $10^{-8}$M, $10^{-7}$M, $10^{-6}$M, $10^{-5}$M and $10^{-4}$M, respectively. The experiment result is shown in FIG. 6 with the concentrations represented in log values.

With reference to FIG. 6, as the concentration of lead ion increases from $10^{-12}$M to $10^{-10}$M, the gain measured by the sensing device shows no significant change. In other words, the sensing device is unable to detect a lead ion concentration variation within said range. However, when the lead ion concentration increases to $10^{-9}$M, the gain decreases from approximately 130 μA to approximately 122 μA. Thereafter, the gain shows significant change as the lead ion concentration increases. Until the lead ion concentration is greater than $10^{-6}$M, the gain stops showing significant change. In other words, the sensing device of the present embodiment has a detection limit for lead ion being $10^{-10}$M and a linear range between $10^{-10}$M and $10^{-6}$M, which cover the current regulation for the lead ion content in water (less than 50 ppb; approximately $2.42 \times 10^{-7}$M) in Taiwan. In this way, the sensing device of the present embodiment is not only capable of confirming whether the lead ion concentration in water exceeds the standard value but also accurately measuring the lead ion concentration variation within a range where the standard value is not exceeded. Accordingly, when the lead ion concentration in water shows an abnormal variation, an in-time processing can still be performed before the content exceeds the standard value.

Experiment 4

Figure 7A:
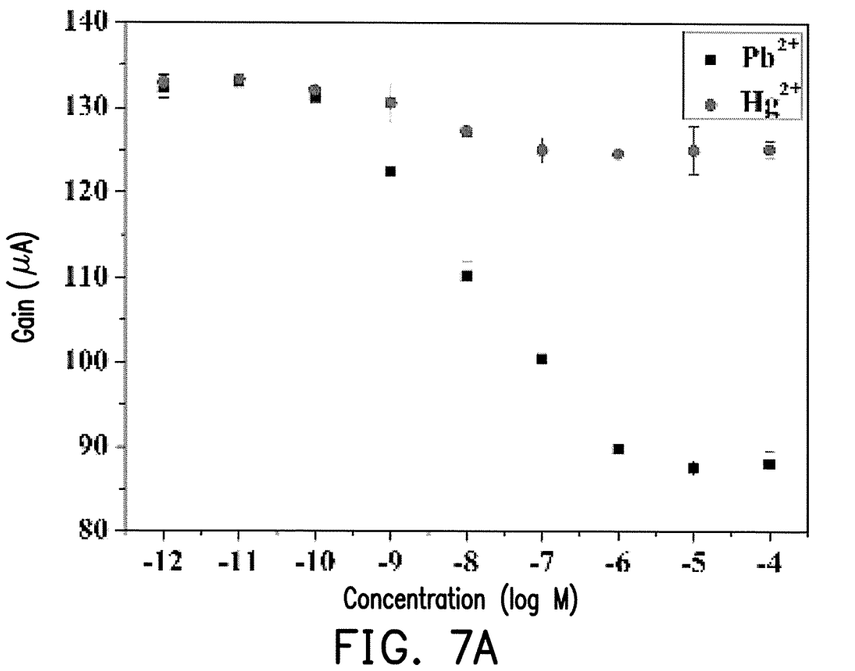
FIG. 7A is a gain-concentration graph obtained by performing an interference test by the sensing device in an embodiment of the invention in Experiment 4.

FIG. 7A is a gain-concentration graph obtained by performing an interference test by the sensing device in an embodiment of the invention in Experiment 4.

In Experiment 4, the interference test is performed by adopting a separate solution method (SSM) with mercury ion ($Hg^{2+}$) as the interference substance. Test solutions used in Experiment 4 are test solutions containing different mercury ion concentrations, which are prepared by dissolving different amounts of mercury dinitrate by a phosphate buffer solution at pH 7 diluted 100 times (0.01×PBS), wherein the mercury ion concentrations are $10^{-12}$M, $10^{-11}$M, $10^{-10}$M, $10^{-9}$M, $10^{-8}$M, $10^{-7}$M, $10^{-6}$M, $10^{-5}$M and $10^{-4}$M, respectively. The experiment result is shown in FIG. 7A with the concentrations represented in log values. It should be noted that, in order to describe the result of the interference test more clearly, the detection result in Experiment 3 (i.e., the result of the detection on the different concentrations of lead ion) is also shown in FIG. 7A.

With reference to FIG. 7A, as the concentration of mercury ion changes, the variation of the gain is far smaller than the variation of the gain in the detection for lead ion. In other words, with use of different ion selective membranes, the sensing device can provide a favorable selectivity which prevents the detected result of the test object to be analyzed from being affected by other interferences in water.

Experiment 5

Figure 7B:
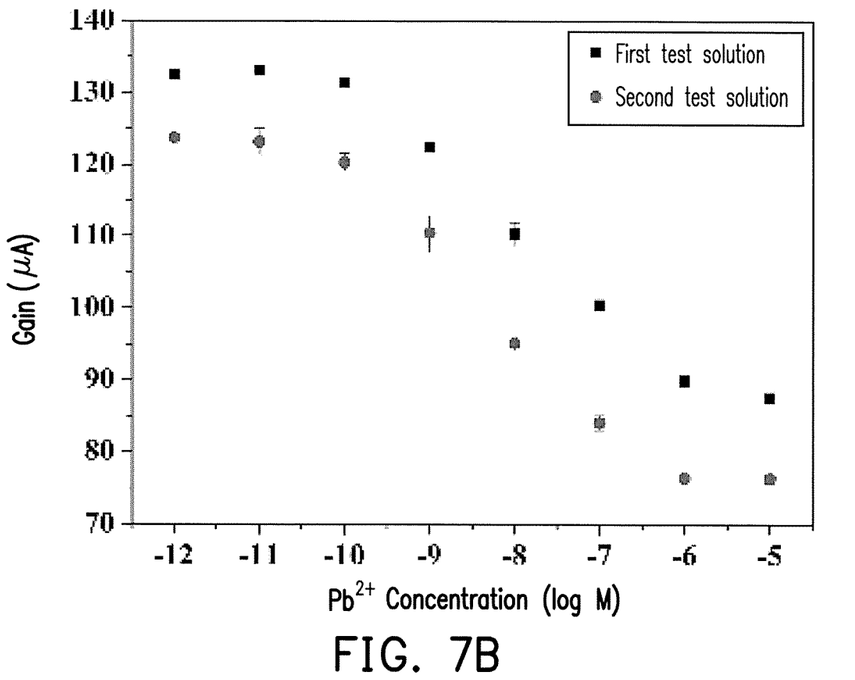
FIG. 7B is a gain-concentration graph obtained by performing an interference test by the sensing device in an embodiment of the invention in Experiment 5.

FIG. 7B is a gain-concentration graph obtained by performing an interference test by the sensing device in an embodiment of the invention in Experiment 5.

In Experiment 5, the interference test is performed by adopting a fix interference method (FIM) with mercury ion ($Hg^{2+}$) as the interference substance. In Experiment 5, two different kinds of test solutions are used, one of which is referred to as a first test solution containing different lead ion concentrations, which are prepared by dissolving different amounts of lead nitrate by a phosphate buffer solution at pH 7 diluted 100 times (0.01×PBS); the other is referred as to a second test solution containing different lead ion concentrations, which are prepared by dissolving different amounts of lead nitrate by a 0.01×PBS at pH 7 containing mercury ion with a concentration of $10^{-5}$M. The lead ion concentrations in the first test solution and the second test solution are $10^{-12}$M, $10^{-11}$M, $10^{-10}$M, $10^{-9}$M, $10^{-8}$M, $10^{-7}$M, $10^{-6}$M, $10^{-5}$M and $10^{-4}$M, respectively. The experiment result is shown in FIG. 7B with the concentrations represented in log values.

With reference to FIG. 7B, regardless of whether the lead ion detection is performed with use of the first test solution or the second test solution, the sensing device of the present embodiment has detection limits for lead ion being $10^{-10}$M and linear ranges between $10^{-10}$M to $10^{-6}$M. The only difference is that the overall gain of the second test solution is lower. In other words, even if the water contains the interference substance like mercury ion, the sensing device of the present embodiment can still accurately measure the lead ion concentration variation. Accordingly, it is not required to additionally perform the pretreatment step on the test solution so procedures in the operation of the sensing device may be simplified while reducing the cost required by the operation.

Experiment 6

Figure 8:
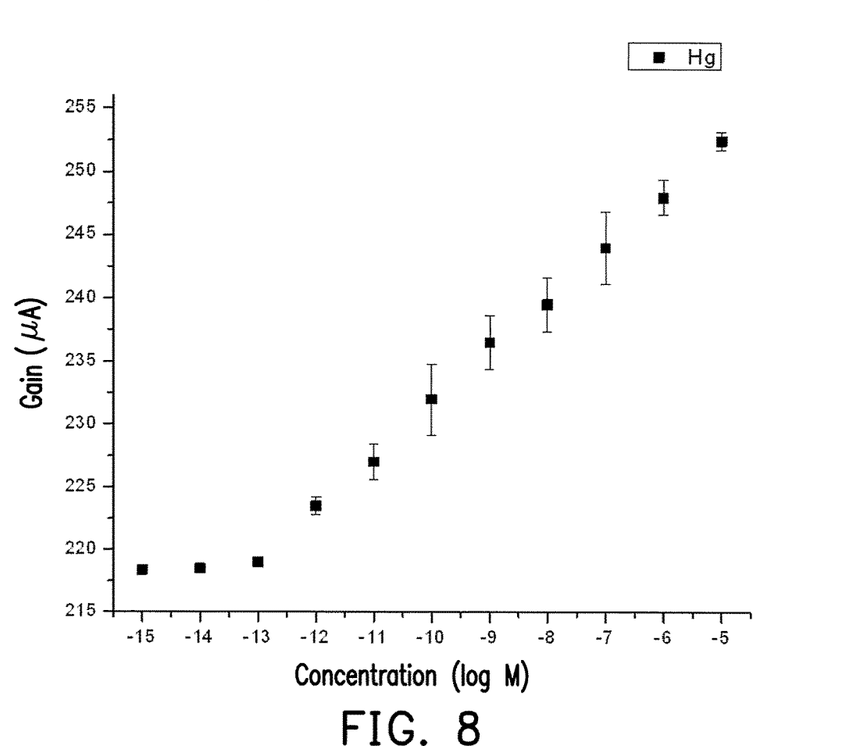
FIG. 8 is a gain-concentration graph obtained by detecting different concentrations of mercury ion by the sensing device in another embodiment of the invention in Experiment 6.

FIG. 8 is a gain-concentration graph obtained by detecting different concentrations of mercury ion by the sensing device in another embodiment of the invention in Experiment 6.

Test solutions used in Experiment 6 are test solutions containing different mercury ion concentrations, which are prepared by dissolving different amounts of mercury dinitrate by a phosphate buffer solution at pH 7 diluted 100 times (0.01×PBS), wherein the mercury ion concentrations are $10^{-15}$M, $10^{-14}$M, $10^{-13}$M, $10^{-12}$M, $10^{-11}$M, $10^{-10}$M, $10^{-9}$M, $10^{-8}$M, $10^{-7}$M, $10^{-6}$M and $10^{-5}$M, respectively. The experiment result is shown in FIG. 8 with the concentrations represented in log values.

With reference to FIG. 8, as the concentration of mercury ion increases from $10^{-15}$M to $10^{-13}$M, the gain measured by the sensing device show no significant change. In other words, the sensing device is unable to detect a mercury ion concentration variation within said range. However, when the mercury ion concentration increases to $10^{-12}$M, the gain increases from approximately 218 μA to approximately 223 μA. Thereafter, the gain shows significant change as the mercury ion concentration increases. In other word, the sensing device of that embodiment has a detection limit for mercury ion being $10^{-13}$M and a linear range between $10^{-13}$M and $10^{-5}$M, which cover the current regulation for the mercury ion content in water (less than 50 ppb; approximately 10 ppb; approximately $4.99 \times 10^{-8}$M) in Taiwan. In this way, the sensing device of that embodiment is not only capable of confirming whether the mercury ion concentration in water exceeds the standard value but also accurately measuring the variation of the mercury ion concentration within a range where the standard value is not exceeded. Accordingly, when the mercury ion concentration in water shows an abnormal variation, a in-time processing can still be performed before the content exceeds the standard value.

Experiment 7

Figure 9:
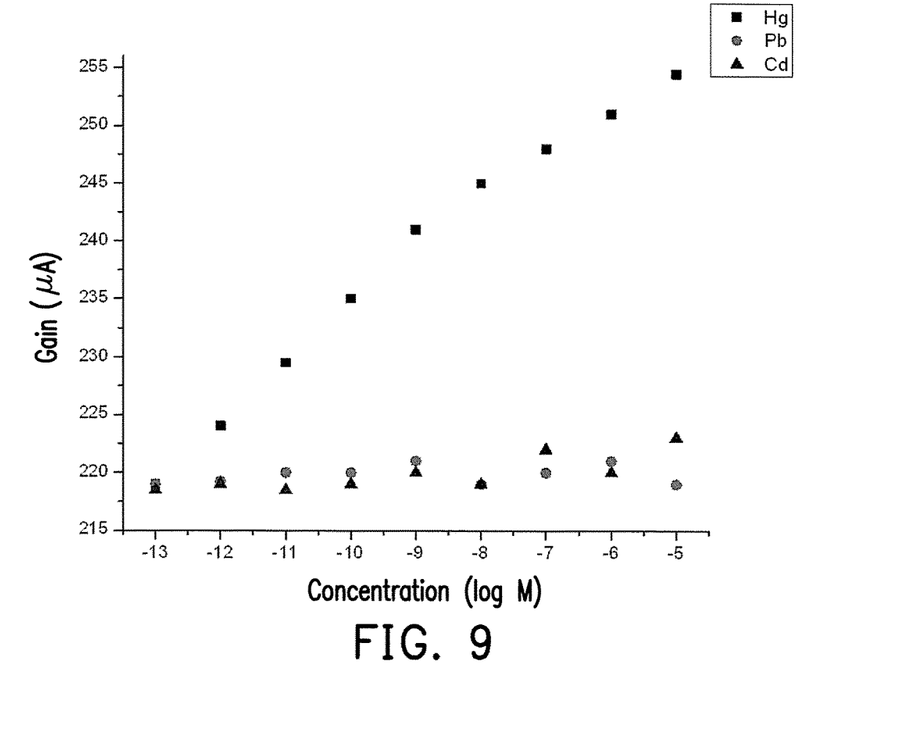
FIG. 9 is a gain-concentration graph obtained by performing a selectivity test by the sensing device in another embodiment of the invention in Experiment 7.

FIG. 9 is a gain-concentration graph obtained by performing a selectivity test by the sensing device in another embodiment of the invention in Experiment 7.

In Experiment 7, measure mercury ion, lead ion and cadmium ion in the test solutions are measured by the sensing device used in Experiment 6 (the sensing device for measuring mercury ion) to confirm whether the sensing device for measuring mercury ion includes the characteristic of high selectivity. In Experiment 7, different concentrations of mercury ion, lead ion and cadmium ion are prepared in a phosphate buffer solution diluted 100 times (0.01×PBS), wherein the concentrations of mercury ion, lead ion and cadmium ion are $10^{-13}$M, $10^{-12}$M, $10^{-11}$M, $10^{-10}$M, $10^{-9}$M, $10^{-8}$M, $10^{-7}$M, $10^{-6}$M and $10^{-5}$M, respectively. The experiment result is shown in FIG. 9 with the concentrations represented in log values.

With reference to FIG. 9, as the concentrations of lead ion and cadmium ion increase (the concentrations increase from $10^{-13}$M to $10^{-5}$M), the gains of the two show no significant change. On the other hand, as the concentration of mercury ion increases, the gain shows significant change. In other words, the sensing device in that embodiment can provide the high selectivity for mercury ion. In this way, even if the water contains the interference substance like lead ion and cadmium ion, the sensing device of the present embodiment can still accurately measure the mercury ion concentration variation. Accordingly, it is not required to additionally perform the pretreatment step on the test solution so procedures in the operation of the sensing device may be simplified while reducing the cost required by the operation.

Experiment 8

Figure 10A:
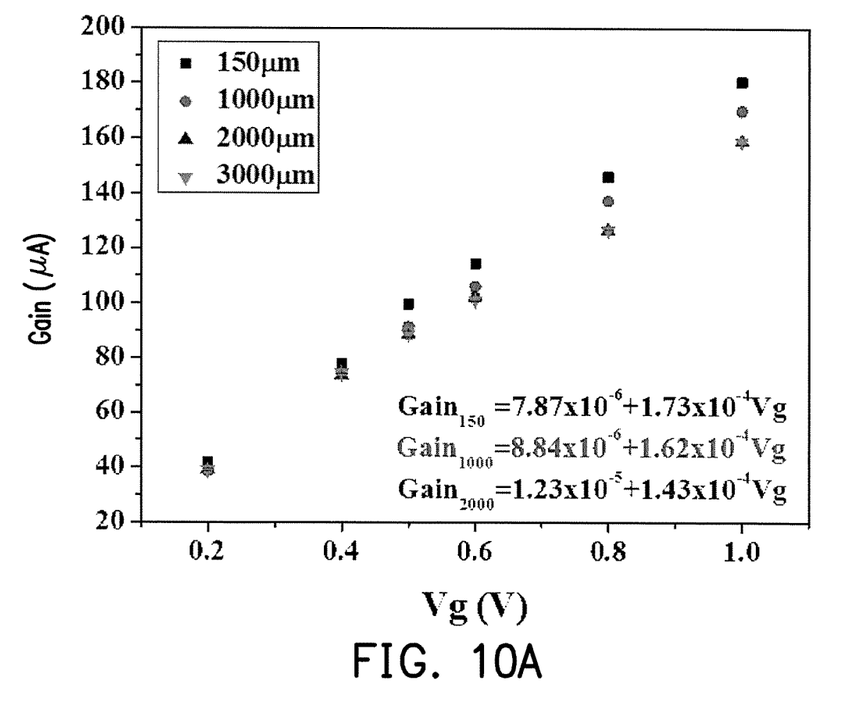
FIG. 10A is a gain-gate voltage graph obtained by performing a sensitivity test on the sensing devices in different embodiments in Experiment 8.

FIG. 10A is a gain (Gain)-gate voltage (Vg) graph obtained by performing a sensitivity test on the sensing devices in different embodiments in Experiment 8.

In Experiment 8, the difference among the sensing devices in the different embodiments is that, a gap between the response electrode and the gate end is different. The gaps of the sensing devices in different embodiments are 150 μm, 1000 μm, 2000 μm and 3000 μm, respectively. In Experiment 8, gains obtained by the sensing devices in said different embodiments under different gate voltages (Vg) are measured, and linear regression equations of the gains of the sensing devices in the different embodiments versus the gate voltages are derived according to experimental data. The result is shown in FIG. 10A.

With reference to FIG. 10A, the sensing device with the gap between the response electrode and the gate end at 150 μm has the linear regression equation of $Gain_{150}=7.87 \times 10^{-6}+1.73 \times 10^{-4} Vg$; the sensing device with the gap between the response electrode and the gate end at 1000 μm has the linear regression equation of $Gain_{1000}=8.84 \times 10^{-6}+1.62 \times 10^{-4} Vg$; the sensing device with the gap between the response electrode and the gate end at 2000 μm has the linear regression equation of $Gain_{2000}=1.23 \times 10^{-5}+1.43 \times 10^{-4} Vg$. In view of the above, it can be known that, when the gap between the response electrode and the gate end is greater than 2000 μm, a slope of the gain versus gate voltage shows no significant change. However, when the gap between the response electrode and the gate end is between 150 μm and 1000 μm, the slope of the gain versus gate voltage increases as the gap is reduced.

Experiment 9

Figure 10B:
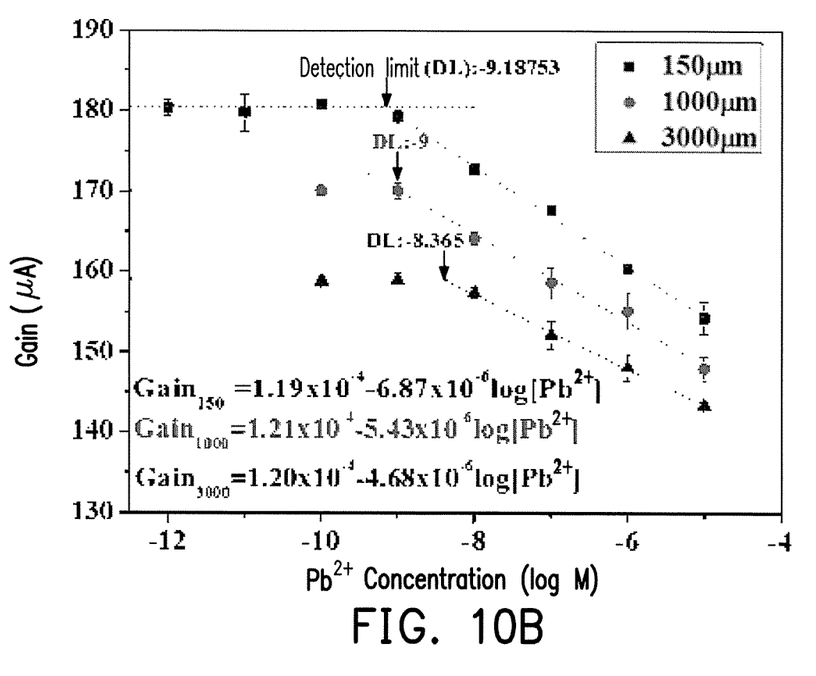
FIG. 10B is a gain-lead ion concentration graph obtained by performing a lead ion concentration detection on the sensing devices in different embodiments in Experiment 9.

FIG. 10B is a gain-lead ion concentration ($Pb^{2+}$ concentration) graph obtained by performing a lead ion concentration detection by the sensing devices in different embodiments in Experiment 9.

In Experiment 9, the difference among the sensing devices in the different embodiments is that, a gap between the response electrode and the gate end is different. The gaps of the sensing devices in different embodiments are 150 μm, 1000 μm and 3000 μm, respectively. In Experiment 9, gains obtained by the sensing devices in said different embodiments under different lead ion concentrations are measured, and linear regression equations of the gains of the sensing devices in the different embodiments versus the concentrations are derived according to experimental data, wherein the lead ion concentrations are $10^{-12}$M, $10^{-11}$M, $10^{-10}$M, $10^{-9}$M, $10^{-8}$M, $10^{-7}$M, $10^{-6}$M and $10^{-5}$M, respectively (in 0.02×PBS). The experiment result is shown in FIG. 10B with the concentrations represented in log values.

With reference to FIG. 10B, the sensing device with the gap between the response electrode and the gate end at 150 μm has the linear regression equation of $Gain_{150}=1.19 \times$ $10^{-4}$–$6.57\times10^{-6}$ log[$Pb^{2+}$] and the detection limit (DL) being –9.18753(log M); the sensing device with the gap between the response electrode and the gate end at 1000 μm has the linear regression equation of Gain$_{1000}$=1.21×10$^{-4}$– 5.43×10$^{-6}$ log[$Pb^{2+}$] and the detection limit being –9(log M); the sensing device with the gap between the response electrode and the gate end at 3000 μM has the linear regression equation of Gain$_{3000}$=1.20×10$^{-4}$–4.68×10$^{-6}$ log [$Pb^{2+}$] and the detection limit being –8.365(log M). In view of the above, it can be known that, the sensing devices with the gap between the response electrode and the gate end at 150 μM or 1000 μm have the sensitivities significantly higher than the sensitivity of the sensing device with the gap between the response electrode and the gate end at 3000 μm, and have the detection limit greater than the sensing device with the gap at 3000 μm by almost one order.

Figure 10C:
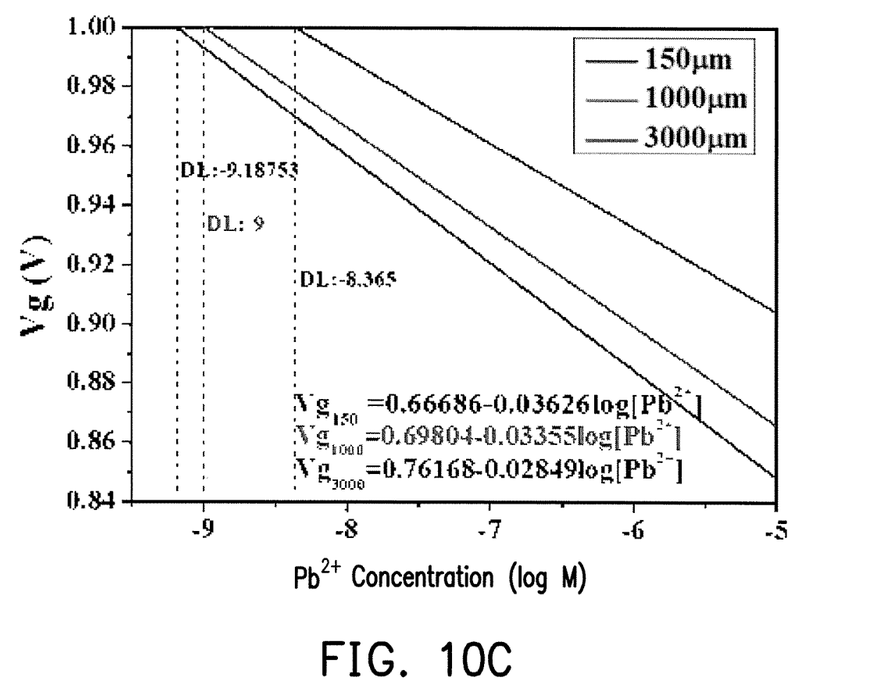
FIG. 10C is a gate voltage-lead ion concentration graph for the sensing devices in different embodiments derived from data in Experiment 8 and Experiment 9.

FIG. 10C is a gate voltage (Vg)-lead ion concentration ($Pb^{2+}$ concentration) graph for the sensing devices in different embodiments derived from data in Experiment 8 and Experiment 9.

With reference to FIG. 10C, the sensing device with the gap between the response electrode and the gate end at 150 μm has the linear regression equation of Vg$_{150}$=0.66686– 0.03626 log[$Pb^{2+}$] and the detection limit being –9.18753 log M; the sensing device with the gap between the response electrode and the gate end at 1000 μm has the linear regression equation of Vg$_{1000}$=0.69804–0.03355 log[$Pb^{2+}$] and the detection limit being –9 log M; the sensing device with the gap between the response electrode and the gate end at 3000 μm has the linear regression equation of Vg$_{3000}$=0.76168–0.02849 log[$Pb^{2+}$] and the detection limit being –8.365 log M. In view of the above, it can be known that, the sensing devices with the gap between the response electrode and the gate end at 150 μm or 1000 μm have slopes respectively being –36.26 mV/log[$Pb^{2+}$] and –33.55 mV/log [$Pb^{2+}$], which are greater than the slope (–29.58 mV/log [$Pb^{2+}$]) of the ideal Nernst equation ($E_{ISM,\,ideal}$=c+0.02958 log[$Pb^{2+}$]). In other words, the sensing devices in the foregoing embodiment have the sensitivities surpassing the sensitivity of Nernst limit. Based on the above experiments, a semi-empirical equation can be derived, as shown by Equation 1 below:

$$E_{pb\text{-}ISHEMT}=c+0.02958\eta\,\log[Pb^{2+}] \quad \text{[Equation 1]}$$

In Equation 1, $E_{pb\text{-}ISHEMT}$ denotes an electric field applied between the response electrode and the gate end (i.e., the electric field F described above); η is dependent on the gate voltage (Vg) and the gap between the response electrode and the gate end; c is a constant. In view of Equation 1, it can be known that, the electric field between the sensing electrode and the gate end (in the solution) is highly related to the sensitivity of the sensing device (the sensitivity is higher if the electric field is higher).

In summary, it can be known that, in the sensing device and the ion detection method proposed in the foregoing embodiments, because the response electrode is disposed opposite to the gate end of the transistor and spaced apart from the transistor, the sensing device can have the characteristics of the low detection limit and the high sensitivity. Further, because the selective membrane is located on the response electrode or on the transistor, the sensing device can provide the high selectivity for the test object to be measured.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A sensing device, comprising:
   a transistor, comprising a gate end, a source end, a drain end, and a semiconductor layer, wherein the source end and the drain end are located on the semiconductor layer, and the gate end is located between the source end and the drain end;
   at least one response electrode, disposed opposite to the gate end of the transistor and spaced apart from the transistor, and the at least one response electrode comprises a response layer; and
   a selective membrane, located on a surface of the response layer of the at least one response electrode adjacent to the transistor, wherein the selective membrane has a selectivity for a test object, and the selective membrane prevents an interference substance from approaching the surface of the response layer of the at least one response electrode,
   wherein the semiconductor layer comprises a first semiconductor layer and a second semiconductor layer disposed on the first semiconductor layer, and an area of a top surface of the second semiconductor layer is less than an area of a top surface of the first semiconductor layer so as to expose a part of the top surface of the first semiconductor layer,
   wherein the source end and the drain end are respectively located on two opposite sidewalls of the second semiconductor layer and on the top surface of the first semiconductor layer, and the part of the top surface of the first semiconductor layer is in contact with the source end and the drain end,
   wherein a material of the semiconductor layer is GaN, AlInN, AlGaN or a combination thereof, and a gap between the at least one response electrode and the gate end is 150 μm to 3000 μm,
   wherein the at least one response electrode is physically separated from the transistor, and the at least one response electrode does not contact the source end and the drain end.

2. The sensing device according to claim 1, wherein an electric field between the at least one response electrode and the gate end of the transistor is F when a voltage is applied to the at least one response electrode, and F≤1 mV/cm.

3. The sensing device according to claim 1, wherein the at least one response electrode comprising a plurality of response electrodes, and the plurality of response electrodes are spaced apart from each other.

4. The sensing device according to claim 3, further comprising:
   a plurality of switch circuits, each of the plurality of response electrodes being connected to each of the plurality of switch circuits.

5. The sensing device according to claim 1, wherein the at least one response electrode is separately disposed above the gate end of the transistor.

6. The sensing device according to claim 1, wherein the at least one response electrode and the gate end of the transistor are located on a same plane.

7. The sensing device according to claim 1, wherein the transistor comprises a high electron mobility transistor, a silicon-based field effect transistor, a nanowire field effect transistor, a carbon nanotube field effect transistor, a graphene field effect transistor or a molybdenum disulfide field effect transistor.

8. The sensing device according to claim 1, wherein the selective membrane comprises an ion selective membrane, a molecular selective membrane, a gas selective membrane or a combination thereof.

9. The sensing device according to claim 8, wherein the ion selective membrane comprises an ionophore, an ionic complex, a plasticizer, a polymeric material or a combination thereof.

10. An ion detection method, comprising:
providing the sensing device according to claim 1;
placing a test solution onto the selective membrane; and
applying a voltage to the at least one response electrode to generate an electric field between the at least one response electrode and the gate end of the transistor, and measuring a current generated from the transistor to obtain an ion content of the test solution.

11. The ion detection method according to claim 10, wherein the electric field is F, and F≤1 mV/cm.

12. The ion detection method according to claim 10, wherein the at least one response electrode is a plurality of response electrodes, and the plurality of response electrodes are spaced apart from each other.

13. The ion detection method according to claim 12, wherein the sensing device further comprising:
a plurality of switch circuits, each of the plurality of response electrodes being connected to each of the plurality of switch circuits.

14. The ion detection method according to claim 10, wherein the at least one response electrode is separately disposed above the gate end of the transistor.

15. The ion detection method according to claim 10, wherein the at least one response electrode and the gate end of the transistor are formed on a same plane.

16. The ion detection method according to claim 10, wherein the transistor comprises a high electron mobility transistor, a silicon-based field effect transistor, a nanowire field effect transistor, a carbon nanotube field effect transistor, a graphene field effect transistor or a molybdenum disulfide field effect transistor.

17. The ion detection method according to claim 10, wherein the selective membrane comprises an ionophore, an ionic complex, a plasticizer, a polymeric material or a combination thereof.

* * * * *